United States Patent
Chouno

(10) Patent No.: US 8,300,909 B2
(45) Date of Patent: Oct. 30, 2012

(54) ULTRASONOGRAPHIC DEVICE AND ULTRASONOGRAPHIC METHOD

(75) Inventor: Tomoaki Chouno, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 1016 days.

(21) Appl. No.: 12/301,350

(22) PCT Filed: May 14, 2007

(86) PCT No.: PCT/JP2007/059848
§ 371 (c)(1),
(2), (4) Date: Nov. 18, 2008

(87) PCT Pub. No.: WO2007/135884
PCT Pub. Date: Nov. 29, 2007

(65) Prior Publication Data
US 2009/0163812 A1 Jun. 25, 2009

(30) Foreign Application Priority Data
May 19, 2006 (JP) .................................. 2006-139865

(51) Int. Cl.
*G06K 9/00* (2006.01)
(52) U.S. Cl. ........................................ 382/128; 382/199
(58) Field of Classification Search .................. 382/128, 382/199; 128/922; 600/437
See application file for complete search history.

(56) References Cited

U.S. PATENT DOCUMENTS

| | | | | |
|---|---|---|---|---|
| 5,469,850 | A | 11/1995 | Iizuka et al. | 128/660.07 |
| 5,664,572 | A | 9/1997 | Kishimoto | 128/660.07 |
| 2005/0143655 | A1 | 6/2005 | Satoh | 600/443 |
| 2006/0002624 | A1* | 1/2006 | Tamura | 382/266 |

FOREIGN PATENT DOCUMENTS

| | | |
|---|---|---|
| JP | 08-206117 A | 8/1996 |
| JP | 09-094248 A | 4/1997 |
| JP | 2005-205199 A | 8/2005 |

* cited by examiner

*Primary Examiner* — Andrew W Johns
(74) *Attorney, Agent, or Firm* — Antonelli, Terry, Stout & Kraus, LLP.

(57) ABSTRACT

An ultrasonographic device is equipped with selecting means for selecting a site for detecting the position of a boundary of an organ of the examinee on the ultrasonic image displayed on the display means, boundary extracting filter setting means for setting a boundary extracting filter comprising two areas which are spaced from each other at a predetermined interval on the ultrasonic image, and boundary position detecting means for analyzing pixel data within the boundary extracting filter set by the boundary extracting filter setting means in the neighborhood of the site selected by the selecting means to detect the position of the boundary, the boundary position detected by the boundary position detecting means being displayed on the display means under the control of the control means.

20 Claims, 14 Drawing Sheets

FIG.6
(a)
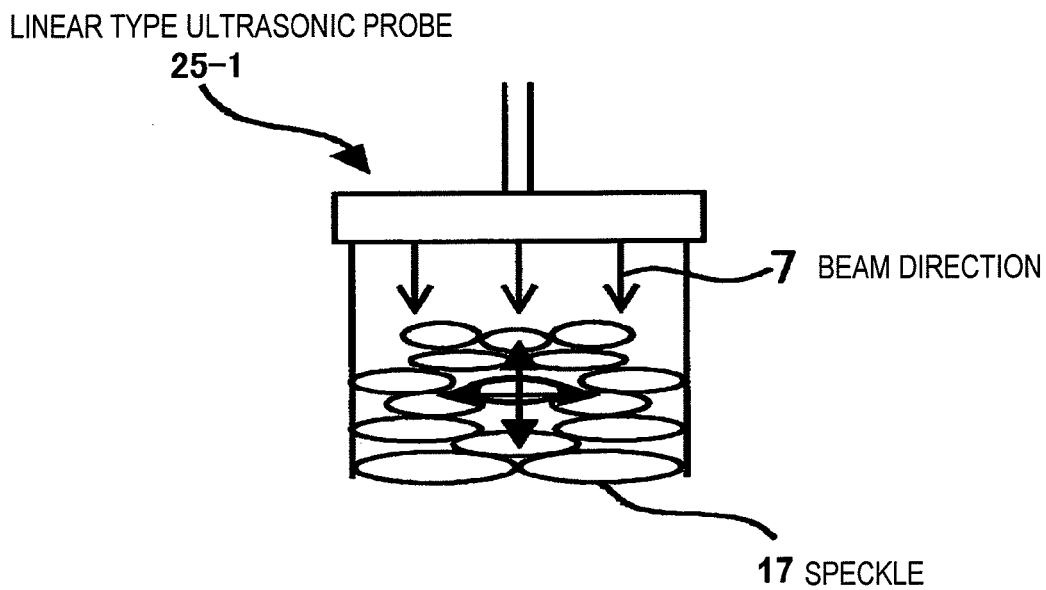
(b)
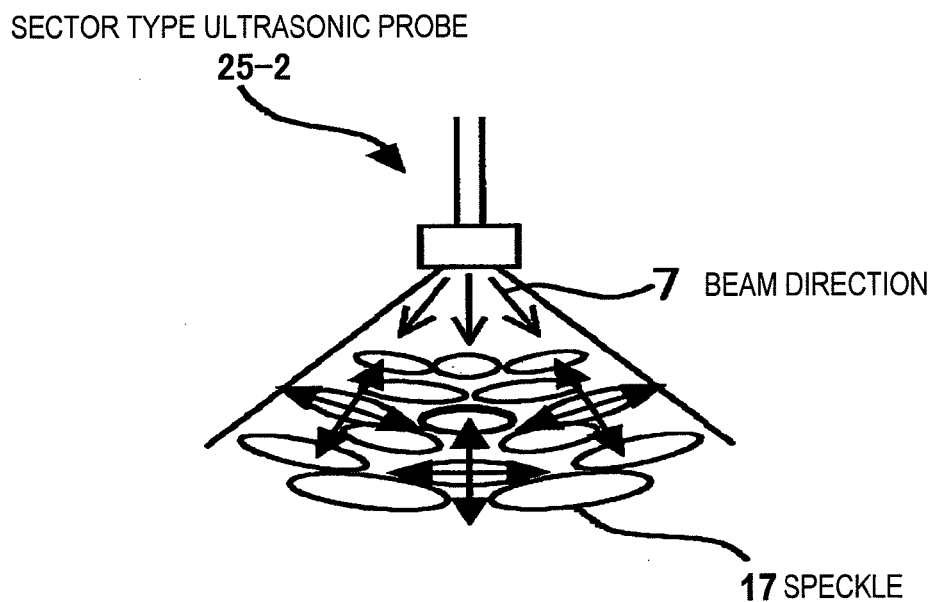

FIG.7
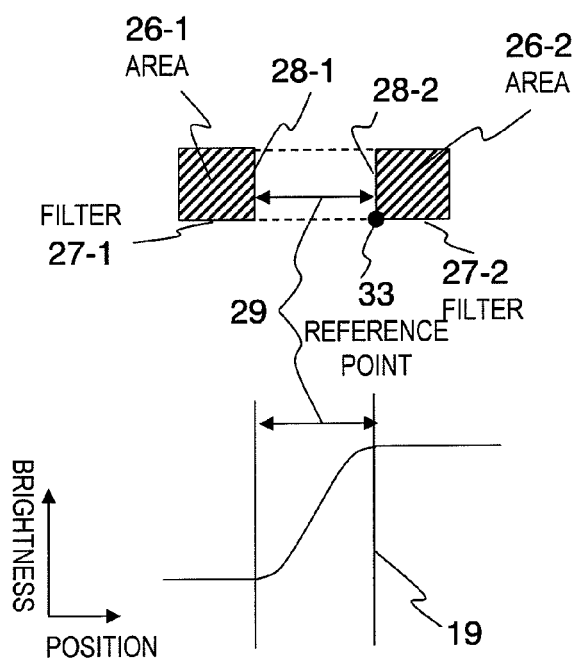 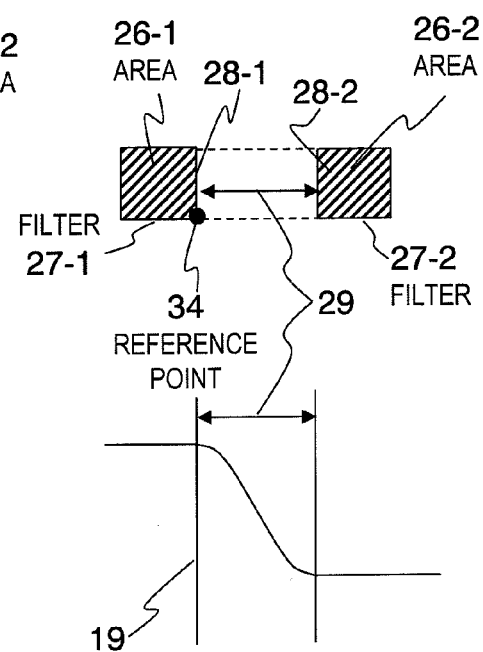

FIG.15
FILTER
46-1
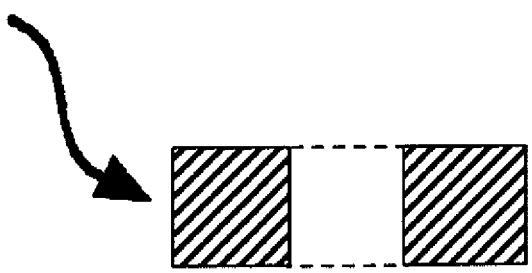
46-2
46-3
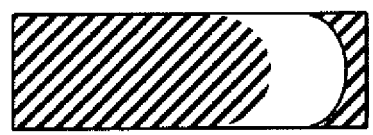

ULTRASONOGRAPHIC DEVICE AND ULTRASONOGRAPHIC METHOD

TECHNICAL FIELD

The present invention relates to an ultrasonographic device and an ultrasonographic method, and particularly to an ultrasonographic device and an ultrasonographic method that can accurately extract a boundary (contour) of a target tissue such as an organ or the like.

BACKGROUND ART

In an ultrasonographic diagnosis using an ultrasonographic device, information on a boundary (contour) of an organ or the like to which attention is paid is effective information. For example, with respect to an organ such as a heart or the like, it is effective to diagnosis that a boundary (contour) of the left ventricle is extracted and the area surrounded by the boundary (contour) concerned is determined or the volume of the left ventricle is estimated on the basis of the boundary (contour).

For example, a prior art described in Patent Document 1 is known as a technique of extracting and displaying a boundary (contour) of a tissue.

Patent Document 1: JP-A-8-206117

According to the prior art disclosed in the Patent Document 1, the local maximum point of a scalar quantity representing the gradient of an image signal at each point in a tomogram is determined and the boundary (contour) of the tissue is drawn from the local maximum points.

DISCLOSURE OF THE INVENTION

Problem to be Solved by the Invention

However, the inventors have reviewed the prior art, and consequently have found the following problem.

That is, a noise called as a speckle noise is contained in an ultrasonographic image. It is considered that this speckle noise appears because scattering waves caused by a reflectors in a biomedical tissue which is sufficiently smaller than the wavelength of ultrasonic wave generate at various phases and interfere in one another (see Patent Document 2 as a prior art concerning the speckle noise).

Patent Document 2: JP-A-09-94248

According to the prior art described in Patent Document 1, the boundary (contour) of an organ is extracted from local maximum points of the scalar quantity representing the gradient, and thus the effect of blurring caused by the speckle noise is not considered. Therefore, there occurs such a problem that the boundary is extracted at the boundary (contour) of an organ under the state that a higher pixel density area protrudes into a lower pixel density area by the amount corresponding to a blurring width. For example, when the boundary of the left ventricle of a heart is extracted, the wall of the heart protrudes into the inside of the heart by the amount corresponding to a blurring width, and thus there occurs a problem that the size of the left ventricle is smaller than the actual size.

Means of Solving the Problem

According to the present invention, an ultrasonographic device having an ultrasonic probe for transmitting/receiving an ultrasonic wave to an examinee, image generating means which is connected to the ultrasonic probe and generates an ultrasonic image on the basis of an ultrasonic signal obtained by the ultrasonic probe, a controller which is connected to the ultrasonic probe and the image generating means to control the ultrasonic probe and the image generating means, and display means which is connected to the image generating means and the controller and displays the ultrasonic image generated by the image generating means under the control of the controller, is characterized by further comprising selecting means for selecting a site for detecting the position of a boundary of an organ of the examinee on the image displayed on the display means, boundary extracting filter setting means for setting a boundary extracting filter comprising two areas which are spaced from each other at a predetermined interval on the ultrasonic image, and boundary position detecting means for analyzing pixel data within the boundary extracting filter set by the boundary extracting filter setting means in the neighborhood of the site selected by the selecting means to detect the position of the boundary, the boundary position detected by the boundary position detecting means being displayed on the display means under the control of the controller.

Furthermore, according to the present invention, an ultrasonographic method that can extract the position of a boundary of an organ displayed on an ultrasonic image comprises:

(1) a step of indicating a site for extracting the boundary on the ultrasonic image;

(2) a step of calculating a blurring width of an image in the neighborhood of the site set in the step (1);

(3) a step of setting as a boundary extracting filter two areas having a gap corresponding to the blurring width calculated in the step (2);

(4) a step of determining the intensity of the boundary by analyzing pixel values in the two areas while varying the position and/or gradient of the boundary extracting filter set in the step (3);

(5) a step of extracting the position of the boundary by determining the position and/or gradient at which the boundary intensity is maximum or equal to a predetermined value or more in the step (4); and (6) a step of calculating the area of an area surrounded by the boundary or the volume of an organ representing an area surrounded by the boundary on the basis of the boundary position determined in the step (5).

Effect of the Invention

An object of the present invention is to extract an contour with high precision in consideration of a blurring width appearing on an image in an ultrasonographic device for extracting a boundary (contour) of an organ by using an ultrasonic image.

BRIEF DESCRIPTION OF THE DRAWINGS

FIG. 6 is a diagram showing what speckle generates in accordance with the type of an ultrasonic probe being used.

FIG. 7 is a filter shape of a boundary extraction filter having two areas.

FIG. 15 is a diagram showing an example when the shapes of the two filter areas are changed.

Figure 1:
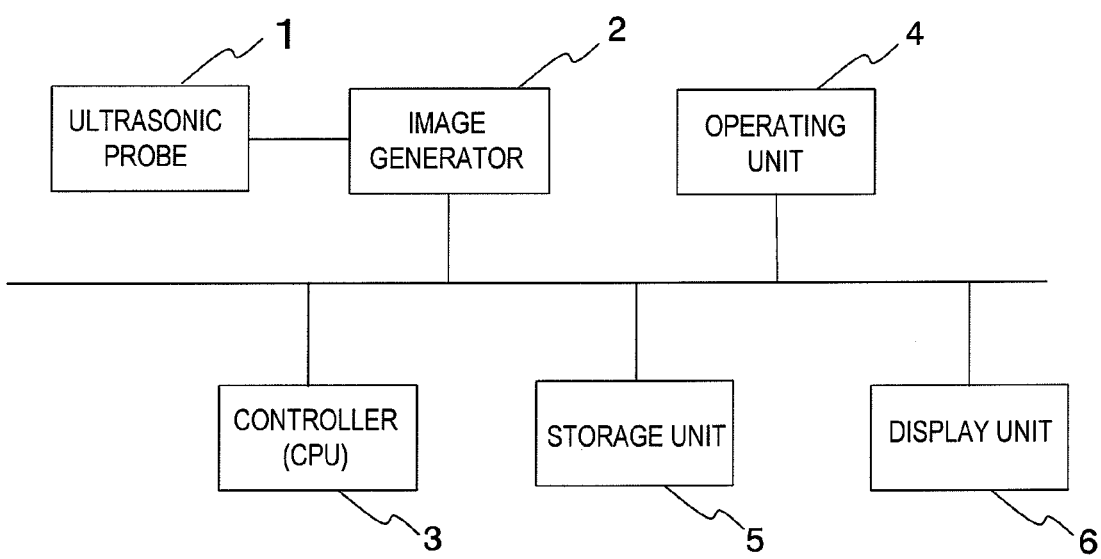
FIG. 1 is a block diagram showing the overall construction of an ultrasonographic device according to an embodiment 1 of the present invention.

DESCRIPTION OF REFERENCE NUMERALS 7 boundary extracting site indicating means, 8 boundary extraction calculating means, 9 organ measuring means, 10 image blurring width calculating means, 11 filter shape creating/deforming means, 12 boundary intensity calculating means, 13 boundary position detecting means

BEST MODES FOR CARRYING OUT THE INVENTION

An ultrasonographic device according to embodiments of the present invention will be described with reference to the drawings.

Embodiment 1

FIG. 1 is a block diagram showing the overall construction of an ultrasonographic device according to an embodiment 1 of the present invention.

According to FIG. 1, the ultrasonographic device comprises an ultrasonic probe 1 for transmitting/receiving an ultrasonic wave, an image generator 2 which is connected to the ultrasonic probe 1 and generates an ultrasonic image on the basis of an ultrasonic signal received by the ultrasonic probe, a controller 3 such as CPU (Central Processing Unit) which is connected to each constituent element of the ultrasonographic device for controlling the operation of each constituent element and performing calculation processing or the like, an operating unit 4 which is connected to each constituent element of the ultrasonographic device and through which an operator such as a medical staff or the like operates the ultrasonographic device by using input equipment (keyboard, mouse, trackball, touch panel or the like), a storage unit 5 which is connected to each constituent element of the ultrasonographic device and stores image data, programs, etc., and a display unit 6 such as CRT, a liquid crystal display or the like which is connected to each constituent element of the ultrasonographic device and displays an image, a measurement result or the like.

The ultrasonic probe 1 transmits/receives an ultrasonic wave to an examinee, and it may be designed as a linear type in which transducers are linearly arranged, a sector type in which the angle of a beam can be changed by driving transducers with time lags, a convex type in which transducers are arranged in a convex shape and scanning is carried out while shifting the transducer group or the like. The ultrasonic probe 1 converts an ultrasonic wave (ultrasonic echo) reflected and returned from the inside of the tissue of the examinee to an electrical signal, and then transmits the electrical signal to the image generator 2.

The image generator 2 receives as an input signal the signal which is received and converted to the electrical signal by the ultrasonic probe 1, and generates a B mode image. The input signal concerned is passed through a phasing adder, a logarithmic amplifier, an envelope detector, an A/D converter and a scan converter in the image generator 2 and then converted to the B mode image.

The controller 3 loads a control program for the ultrasonographic device which is stored in the storage unit 5 or the like, and executes it. The controller 3 makes an operation instruction to each constituent element of the ultrasonographic device, and performs timing control and operation processing.

The operating unit 4 is an input device such as a keyboard, a mouse, a trackball, a touch panel or the like on the ultrasonographic device, and a diagnosing person such as a medical staff or the like uses the input device to adjust image quality, instruct measurements, input information, etc.

The storage unit 5 is a device for storing image data, the control programs, etc., and it is a hard disk, a general-purpose memory, a frame memory or the like. The image data stored in the storage unit 5 are obtained B mode images and a file having an image format which can be displayed on general PC.

The display unit 6 is a CRT, a liquid crystal display or the like which displays, on a screen, image data and measurement values and images obtained by graphing the measurement values concerned.

Figure 2:
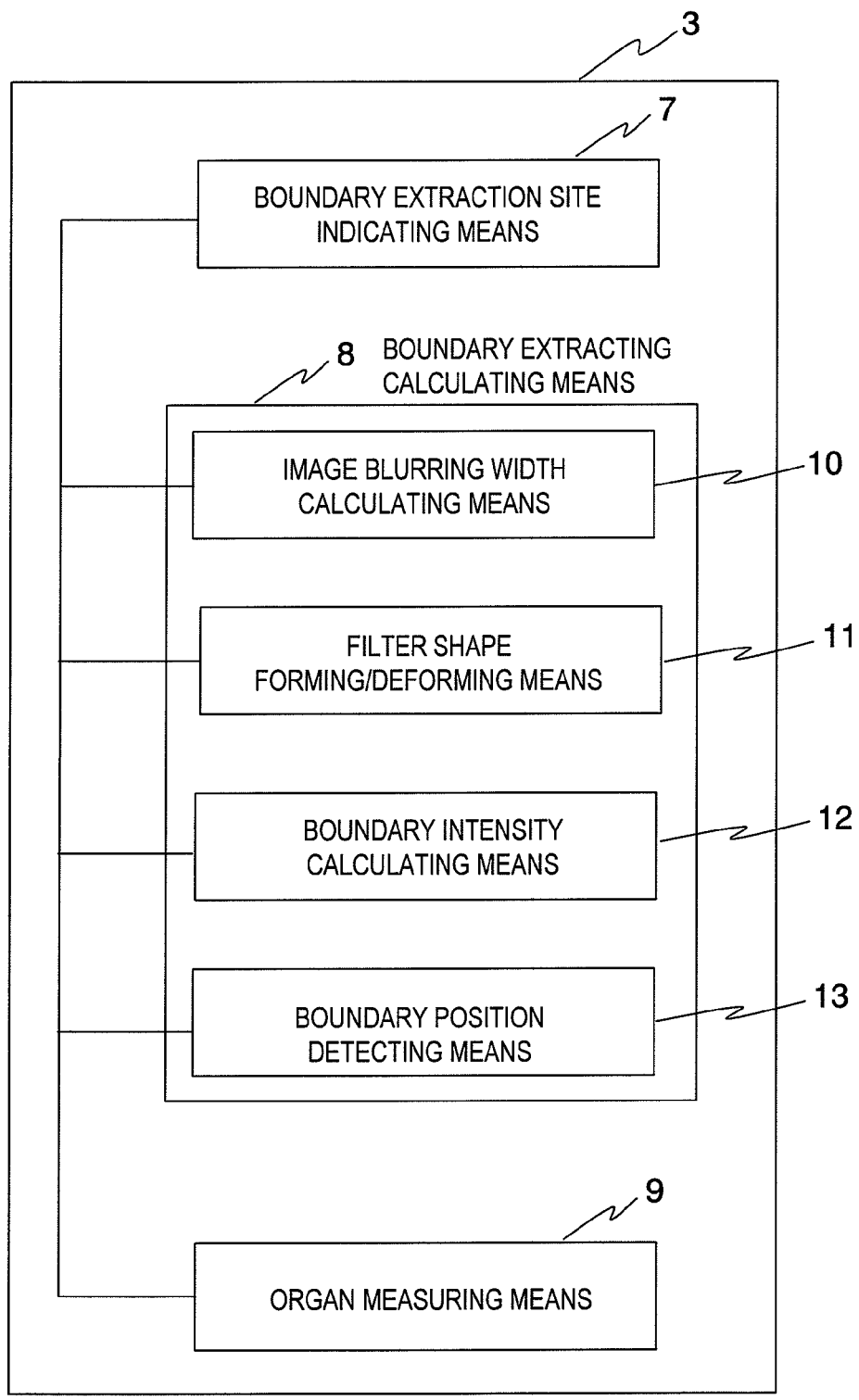
FIG. 2 is a diagram showing the internal of a controller 3.

Furthermore, FIG. 2 shows the inside of the controller 3 according to the embodiment 1 of the present invention. According to FIG. 2, the controller 3 is equipped with boundary extracting site indicating means 7 for indicating a site on an ultrasonic image around which a boundary of an organ should be extracted, boundary extracting calculating means 8 for extracting the boundary of the organ around the site indicated by the boundary extracting site indicating means 7 by calculation, and organ measuring mean 9 for calculating various kinds of physical quantities, that is, the distance such as the size of the organ, etc., the area on the image of the organ, the estimated value of the volume of the organ, etc. on the basis of the boundary extracted by the boundary extracting calculating means 8.

The boundary extracting site indicating means 7 is means for indicating by the input device the neighborhood of a boundary extraction target on the image displayed on the screen of the display unit 6 by an operator. The boundary extraction site indicating mans 7 may execute signal processing on the pixel values of obtained image data to automatically determine the boundary extraction site.

The boundary extracting calculating means 8 calculates an image blurring width of an extraction target image which is indexed in the boundary extraction site indicating means 7, and selects a proper filter in consideration of the image blurring width concerned to detect the boundary position, it comprises the image blurring width calculating means 10, filter shape creating/deforming means 11, boundary intensity calculating means 12 and boundary position detecting means 13.

First, the image blurring width calculating means 10 is means for calculating the size of speckles by using pixel values around the boundary extraction site indicated by the boundary extraction site indicating means 7. A density cooccurrence matrix or an autocorrelation function is used as a method of calculating the size of the speckle.

Next, the filter shape creating/deforming means 11 creates and deforms the boundary extraction filter. For example, the filter shape creating/deforming means 11 creates a filter comprising two areas which are spaced from each other at only the interval corresponding to the distance based on the size of the speckle calculated in the image blurring width calculating means 10. If the shape of a boundary to be extracted is known, the filter shape creating/deforming means 11 may deform the filter shape in conformity with the shape of the boundary concerned.

Next, the boundary intensity calculating means 12 calculates the boundary intensity by using pixel values within two areas at each position and/or gradient, for example, by calculating a separability described later or the like while the position and/or gradient of the boundary extracting filter created by the filter shape creating/deforming means 11 is moved.

Next, the boundary position detecting means 13 detects the position and/or gradient of the boundary extracting filter at which the boundary intensity calculated by the boundary intensity calculating means 12 is equal to the maximum value or a predetermined value or more while moving and scanning the position and/or gradient of the boundary extracting filter. The coordinate value of the boundary position of an extraction target is obtained on the basis of the position of the detected boundary extraction filter.

Furthermore, the organ measuring means 9 calculates various kinds of physical quantities concerning the boundary-extracted organ such as the distance, the area, the volume, etc. by using the coordinate values of the extracted boundary positions. For example, the organ measuring means 9 calculates the physical quantities such as the size of a tumor of an affected area as a target area, etc. with high precision.

Figure 3:
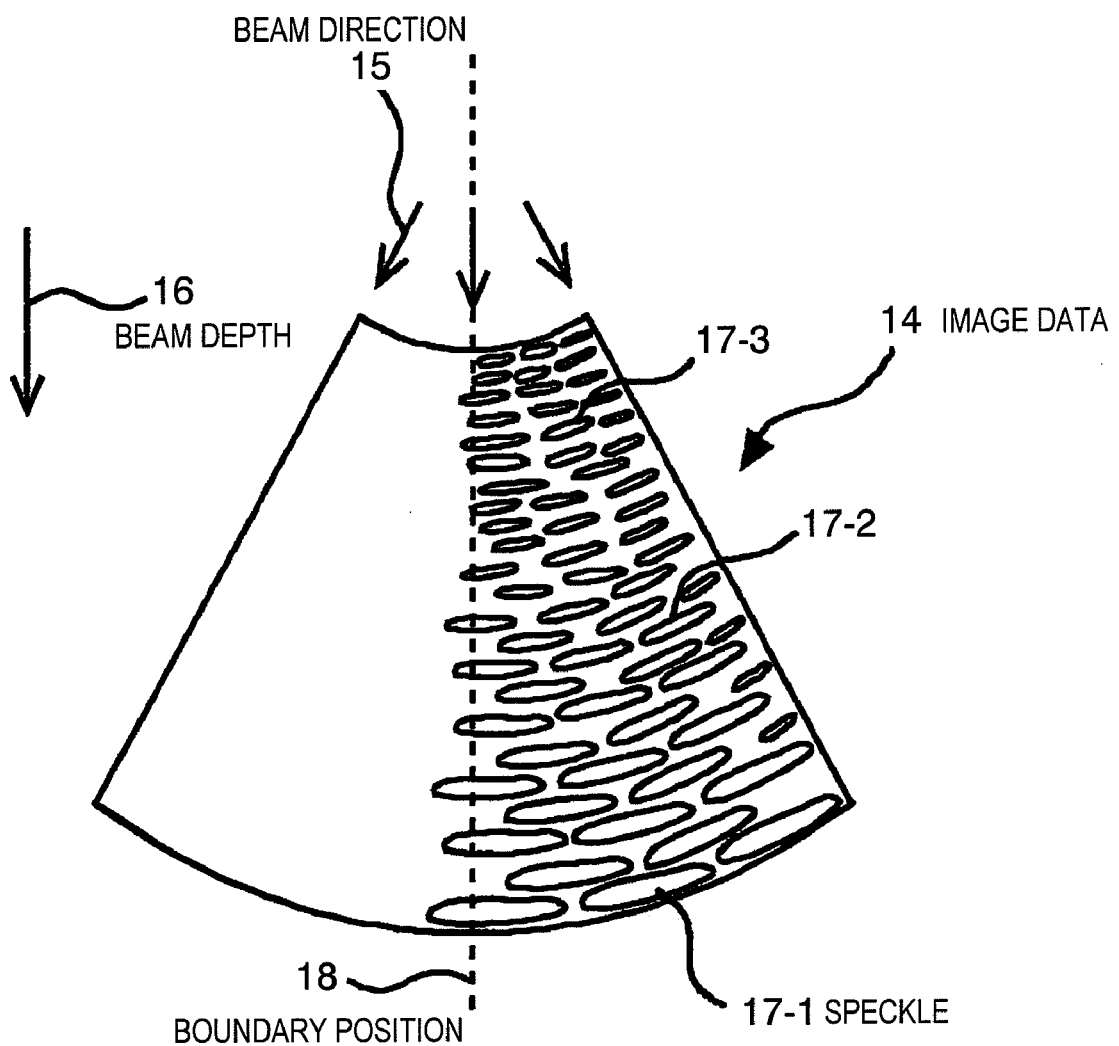
FIG. 3 is a diagram showing an example of image data to be subjected to boundary extraction processing of the embodiment 1.

Next, an example of the image data to be subjected to the boundary extraction processing of the embodiment 1 is shown in FIG. 3. In FIG. 3, 14 represents image data, 15 represents a beam direction, 16 represents a beam depth, 17-1 to 17-3 represent speckles, and 18 represents a boundary position. In 17-1 to 17-3, the speckles are reduced in size in order of 17-1→17-2→17-3, and the depth is shallower. That is, the size of the speckle is larger as the depth is larger.

Figure 4:
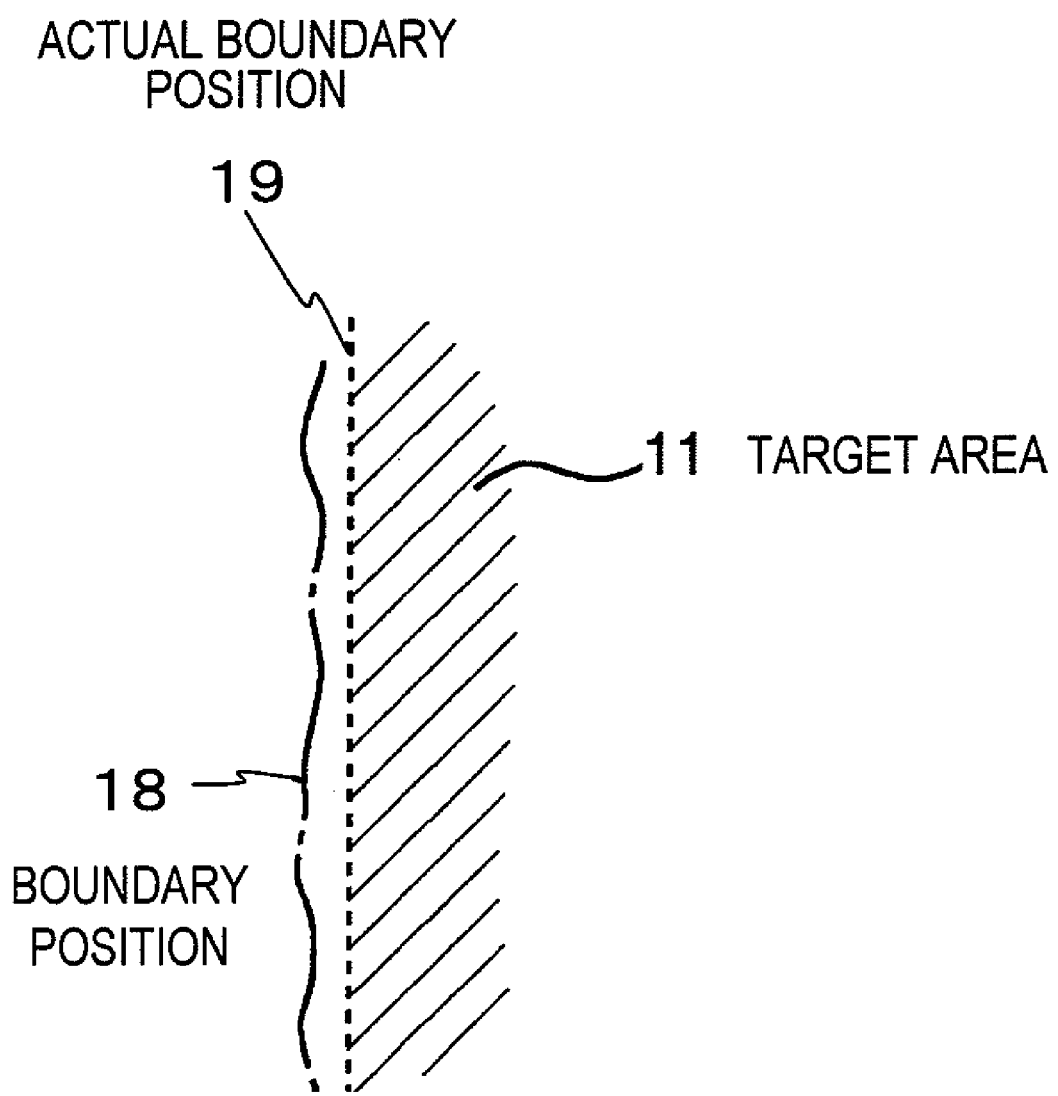
FIG. 4 is a diagram showing the comparison between a boundary position 18 calculated by a conventional method and an actual boundary position 19.

Next, FIG. 4 shows the comparison between the boundary position 18 calculated by the conventional method and the actual boundary position 19. According to FIG. 4, a large error occurs between the boundary position 18 calculated by the conventional method and the actual boundary position 19.

Figure 5:
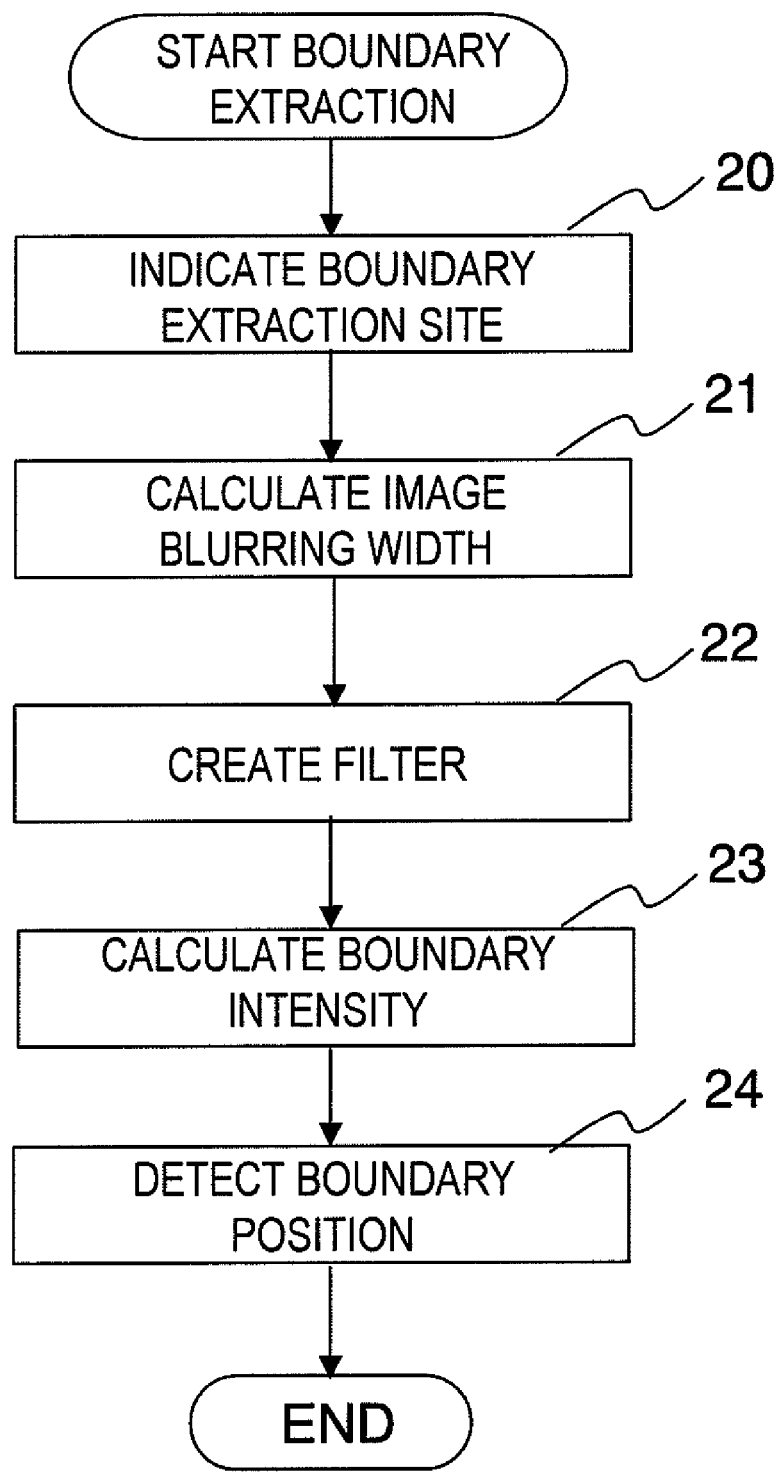
FIG. 5 is a flowchart of the boundary extraction processing according to the embodiment 1.

Next, the flowchart of the boundary extraction processing of the embodiment 1 will be described with reference to FIG. 5.

First, the ultrasonographic device obtains image data 14 by picking up an image of an organ of a patient or the like, and starts boundary extraction of a target area such as the organ concerned or the like by the ultrasonic probe 1 and the image generator 2.

(Step 20)

First, the ultrasonographic device manually or automatically selects and inputs a site as a boundary extraction target by the boundary extracting site indicating means 7.

(Step 21)

Next, the ultrasonographic device calculates a blurring width on an image at the boundary extraction site indicated in step 20 by the image blurring width calculating means 10. Specifically, texture analysis is carried out on pixel value data around the boundary extraction site, and speckles appearing on the image are approximated by elliptical shapes. The half distance of the width (the length in the major axis or minor axis) of each approximated ellipse is defined as a blurring width.

A method of determining a density cooccurrence matrix or an autocorrelation function is used as an example of the texture analysis. (For example, see O. Bassel, et al; "TEXTURE ANALYSIS OF ULTRASONIC IMAGES OF THE PROSTATE BY MEANS OF CO-OCCURRENCE MATRICS." ULTRASONIC IMAGING 15, 218-237 (1993), B. J. Oosterveld et al: "TEXTURE OF B-MODE ECHOGRAMS: 3-D SIMULATIONS AND EXPERIMENTS OF THE EFFECTS OF DIFFRACTION AND SCATTERER DENSITY" ULTRASONIC IMAGING 7, 142-160 (1985)). By executing the texture analysis as described above, the blurring width can be calculated by using only information obtained from the received signal even when parameters concerning the sound field of ultrasonic waves affecting the blurring width in the ultrasonic image (or the distance of the half of the speckle width, for example) are unclear.

Here, FIG. 6 shows what speckle generates in accordance with the type of the ultrasonic probe being used. FIG. 6(a) shows an example of a linear type ultrasonic probe 25-1. With respect to a speckle 17 approximated by an ellipse, the major axis and the minor axis thereof are coincident with the horizontal direction and the vertical direction on the screen. Therefore, when the size of a speckle is extracted by the ellipse approximation, a blurring width is calculated while the directions of the major axis and the minor axis are made coincident with the horizontal direction and the vertical direction on the screen.

On the other hand, FIG. 6(b) shows an example of a sector type ultrasonic probe 25-2. With respect to a speckle 17 approximated by an ellipse, one of the major axis and the minor axis is directed in obliquely on the screen, and it serves as an ultrasonic wave transmission/reception direction. Therefore, when the size of the speckle is extracted by the ellipse approximation, the blurring width is calculated while one of the major axis and the minor axis is made coincident with the oblique direction on the screen, that is, the ultrasonic wave transmission/reception direction.

(Step 22)

Subsequently, a boundary extraction filter having two areas represented by 26-1, 26-2 in FIGS. 7(a), (b) is created by the filter shape/deforming means 11. The boundary extracting filter (27-1, 27-2) in this step comprises the two areas of 26-1, 26-2, and the distance 29 between the confronting sides 28-1, 28-2 of the two areas is equal to the blurring width calculated in step 21.

Figure 8:
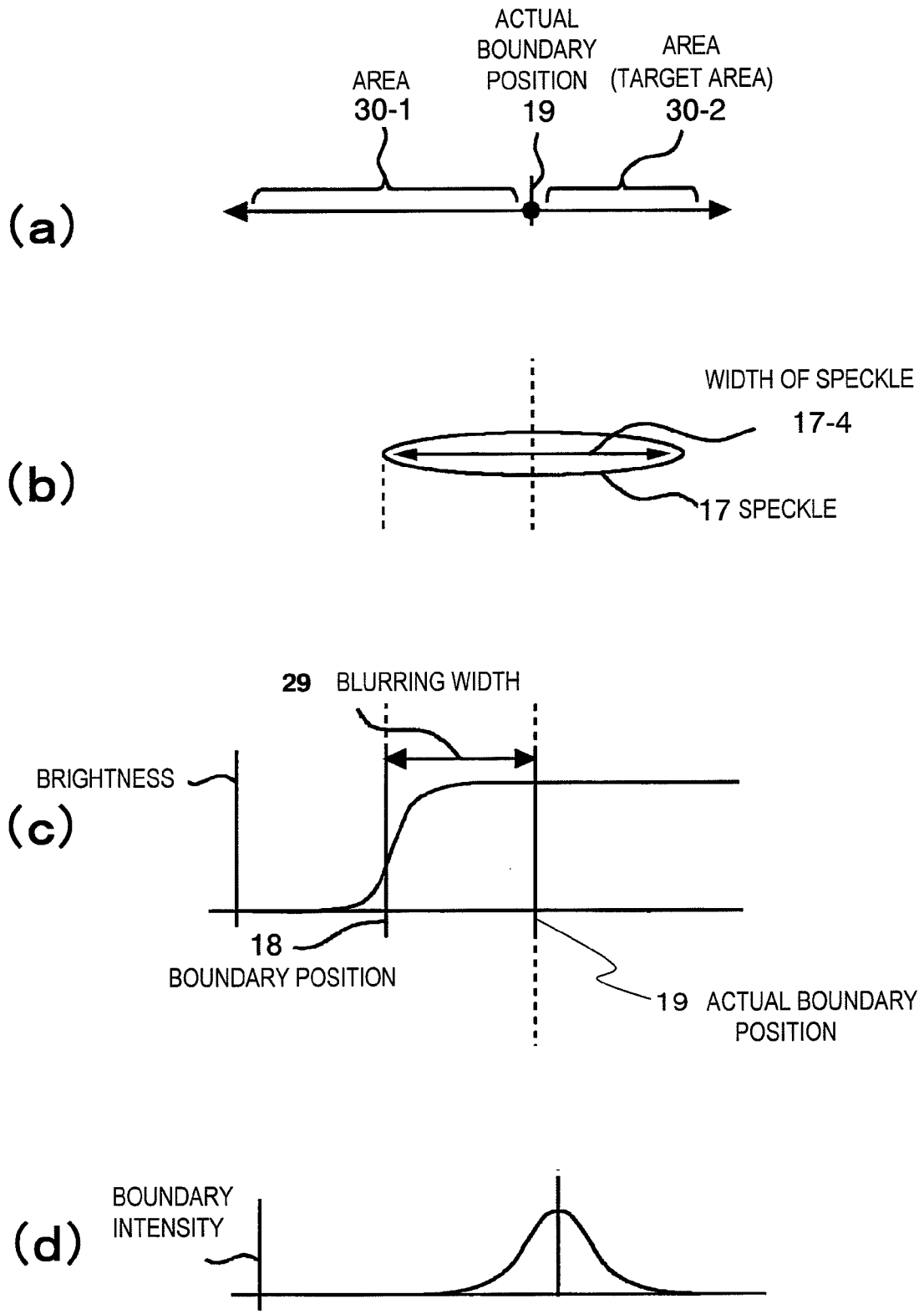
FIG. 8 is a diagram showing how the boundary between two areas 28-1, 28-2 is blurred due to speckles appearing on an image.

Here, it will be described with reference to FIG. 8 how the boundary between two areas 30-1, 30-2 is blurred in accordance with the speckle appearing on the image. First, FIG. 8(a) shows two areas and an actual boundary position 18 located between the areas. FIG. 8(b) shows one of speckles 17 appearing on an image, and 17-4 represents the width of the speckle in the lateral direction of the drawing. FIG. 8(c) shows the profile of an ultrasonic image, and also shows a pixel variation of a line segment traversing the actual boundary position. According to this, it is apparent that the area (30-2) having higher pixel values protrudes to the left side on the drawing because the speckle has a width in the lateral direction on the drawing. When the boundary extraction disclosed in the Patent Document 1 is directly applied by using the profile as shown in FIG. 8(c), the boundary position is extracted at a position different from the original position as represented by 18. Therefore, in order to detect the actual boundary position in this step, a boundary extraction filter must be created so that the position at which a parameter (the intensity described later) for detecting the boundary position is maximum becomes the actual boundary position 19.

The lower sides of FIGS. 7(a), (b) show the same profiles as shown in FIG. 8(c) under the condition that the right side on the drawing at the lower side of FIG. 7(a) shows a case where the pixel value is high and the left side on the drawing at the lower side of FIG. 7(b) shows a case where the pixel value is high. In the boundary extraction filter created in this step, the distance between the confronting sides 28-1, 28-2 in the two areas 26-1, 26-2 is equal to the blurring width of the profile at the lower sides of FIGS. 7(a), (b). This blurring width is determined in step 21, and it is set to the half value of the speckle width in FIG. 8(b), for example.

Figure 9:
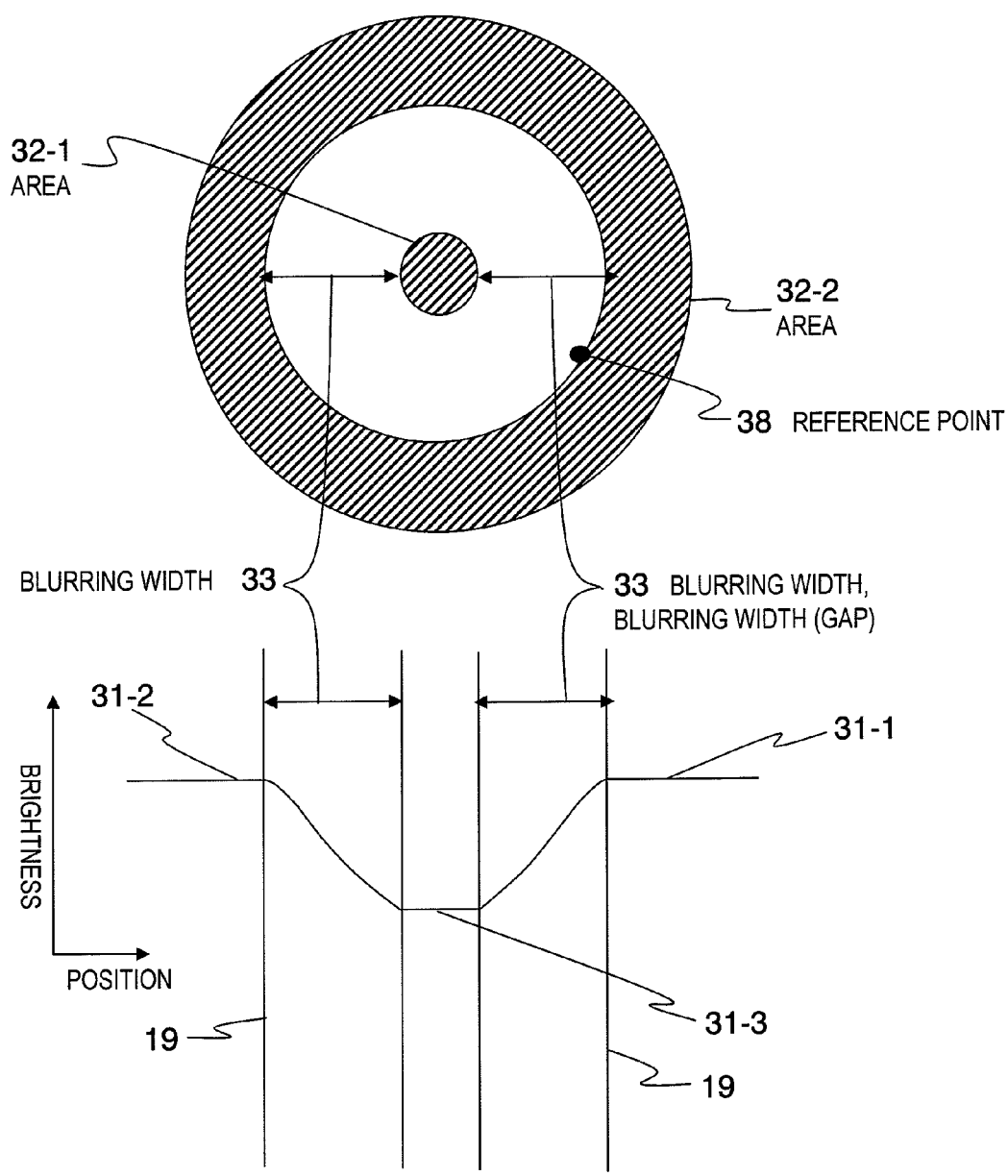
FIG. 9 is a diagram showing a boundary extracting filter created when a boundary formed in a closed area is accurately extracted.

FIG. 9 shows a boundary extraction filter created when a boundary formed by a closed area is accurately extracted. More specifically, as indicated by the profile of pixel values at the lower side of FIG. 9, the boundary between each surrounding area (31-1, 31-2) having high pixel values and an area (31-33) having low pixel values surrounded by the areas (31-1 and 31-2) having the high pixel values is detected.

In this case, as shown at the upper side of FIG. 9, an inner circular area 32-1 and an outer ring-shaped area 32-2 are spaced from each other through the gap 33 corresponding to the blurring width calculated in step 21, thereby creating the boundary extraction filter.

(Step 23)

Subsequently, the boundary creating filter created in the processing of the step 22 is scanned in the image to perform a boundary intensity calculation by the boundary intensity calculating means 12. The boundary intensity calculation will be described in a case where the separability corresponding to the ratio between the interclass variance and the total variance of the two areas described later is used, for example. The interclass variance and the total variance of the two areas is described in Magazine of papers of Institute of Electronics and Communication Engineers of Japan, vol. J63-D, No. 4, pp 349-356. With respect to the interclass variance, the pixel data within the two areas are respectively averaged every area and then the variance value thereof is obtained. With respect to the total variance, the pixel data within the two areas are directly used to determine the variance value. The details of the calculation of the separability in this embodiment will be described by using FIG. 10 and equations (1) to (3).

Figure 10:
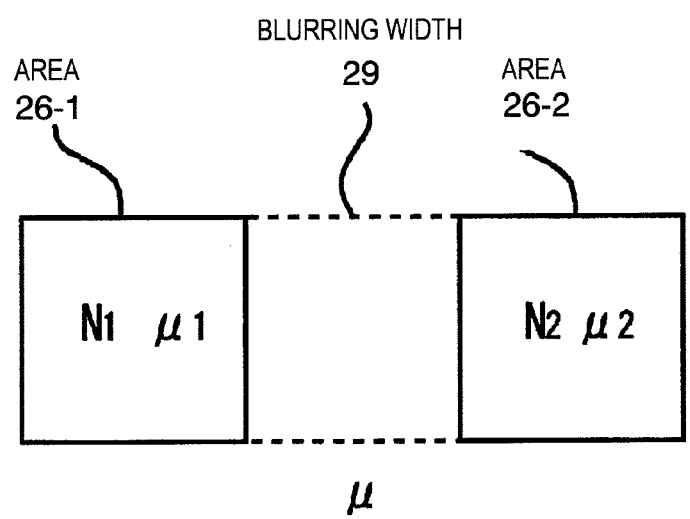
FIG. 10 is a diagram showing a statistical value for calculating a boundary intensity by using a separability.

FIG. 10 is a diagram showing the calculation of a statistical value for calculating the boundary intensity by using the separability, and two areas 26-1 and 26-2 and a blurring width 29 are shown.

As shown in FIG. 10, when the numbers of pixels of the areas 26-1 and 26-2 are represented by $N_1$ and $N_2$, the brightness average value of each area is represented by $\mu_1$, $\mu_2$, the brightness average value of the combined area of the areas 26-1 and 26-2 is represented by and the brightness value of each pixel is defined by Pi ($1 \leq i \leq N_1$, $1 \leq i \leq N_2$), the degree separability $\eta$ is represented by the following equations (1) to (3).

Equation (1)
$$\eta = \sigma_B^2 / \sigma_T^2 \quad (1)$$

Equation (2)
$$\sigma_B^2 = N_1(\mu_1 - \mu)^2 + N_2(\mu_2 - \mu)^2 \quad (2)$$

Equation (3)
$$\sigma_T^2 = \sum_{i=1}^{N_1+N_2} (P_i - \mu)^2 \quad (3)$$

(Step 24)

The equations (1) to (3) are calculated while the boundary extraction filter as indicated by 26-1, 26-2 of FIG. 7 is scanned on the image by moving the boundary extraction filter to various positions and/or with various gradients, and it is calculated how the separability (the boundary intensity) varies. A boundary intensity distribution as shown in FIG. 8(d) is determined, and the position at which the boundary intensity is maximum is determined as an actual boundary position 19 for the detection.

However, the boundary extraction filters shown in FIGS. 7(a) and (b) have the same shape, however, the direction of the area having the high pixel values is different between FIGS. 7(a) and 7(b). Therefore, the extraction boundary position is varied between them. For example, in the case of FIG. 7(a), the right side on the drawing has higher pixel values, and thus the position of an edge of the area 26-2 which is set at the higher pixel-value side out of the two areas constituting the boundary extraction filter and nearer to the other area (26-1) is extracted as a reference point (33) for detecting the boundary position. Furthermore, in the case of FIG. 7(b), the left side on the drawing has higher pixel values, and thus the position of an edge of the area 26-1 which is set at the higher pixel-value side out of the two areas constituting the boundary extraction filter and nearer to the other area (26-2) is extracted as a reference point (34) for detecting the actual boundary position 19.

In a case where a boundary extraction filter created when a boundary formed by a closed area as shown in FIG. 9 is accurately extracted is used, an inside position of the area at the higher pixel-value side (the ring-shaped area 32-2 at the outside in the example of FIG. 9) is extracted as a reference point (35) for detecting the actual boundary position 19.

When the boundary extracting processing of a target area is finished through the processing from the step 20 to the step 24, the determined boundary position (boundary information) is displayed on the display unit 6, the physical quantities such as the size, etc. of the target area are calculated by using the boundary information of the target area whose boundary is extracted by the organ measuring means 9, and the calculation values are displayed and recorded.

According to the ultrasonographic device according to the embodiment 1, the blurring width is calculated from the ultrasonic image, the shape and size of the boundary extraction filter are set on the basis of the blurring width, and the boundary position of the target area is extracted, so that the boundary extraction of the target area can be performed with high precision. More specifically, the boundary extraction filter used in this embodiment comprises two areas, and the width of the gap sandwiched between the two areas is equal to the blurring width calculated from the ultrasonic image. Therefore, in consideration of the blurring width (that is, the distance corresponding to the half of the size of the speckle appearing on the ultrasonic image), the actual boundary position can be extracted with high precision. In the conventional boundary extraction method, the boundary extraction is carried out on the assumption that the pixel value stepwise varies at the boundary, so that the detection precision of the boundary position is lowered as the boundary appearing on the actual image is more dull due to the effect of the speckle or the like. In the present invention, the boundary extraction is carried out on the assumption that the boundary becomes dull due to the effect of the speckle or the like, and thus the boundary position can be always extracted with the same level of accuracy as the case where the boundary on the image is not dull at all times. By using the coordinate of the calculated actual boundary position, the physical quantities such as the size, etc. of the target area can be accurately calculated, and the accurate ultrasonography can be performed by using the calculation values.

The size of the speckle (for example, the amount corresponding to the blurring width) is larger as the image obtaining depth in the examinee is larger. Accordingly, it is desired to vary the interval of the two areas constituting the boundary extraction filter in accordance with the image obtaining depth.

Figure 11:
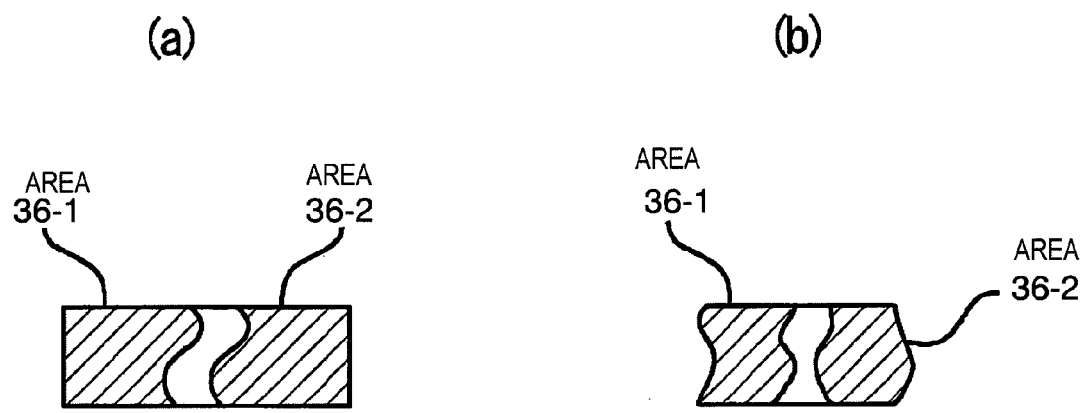
FIG. 11 is a diagram showing a boundary extraction filter which is set to be bent in a gap area between two areas in accordance with bending of an estimated boundary.
Figure 12:
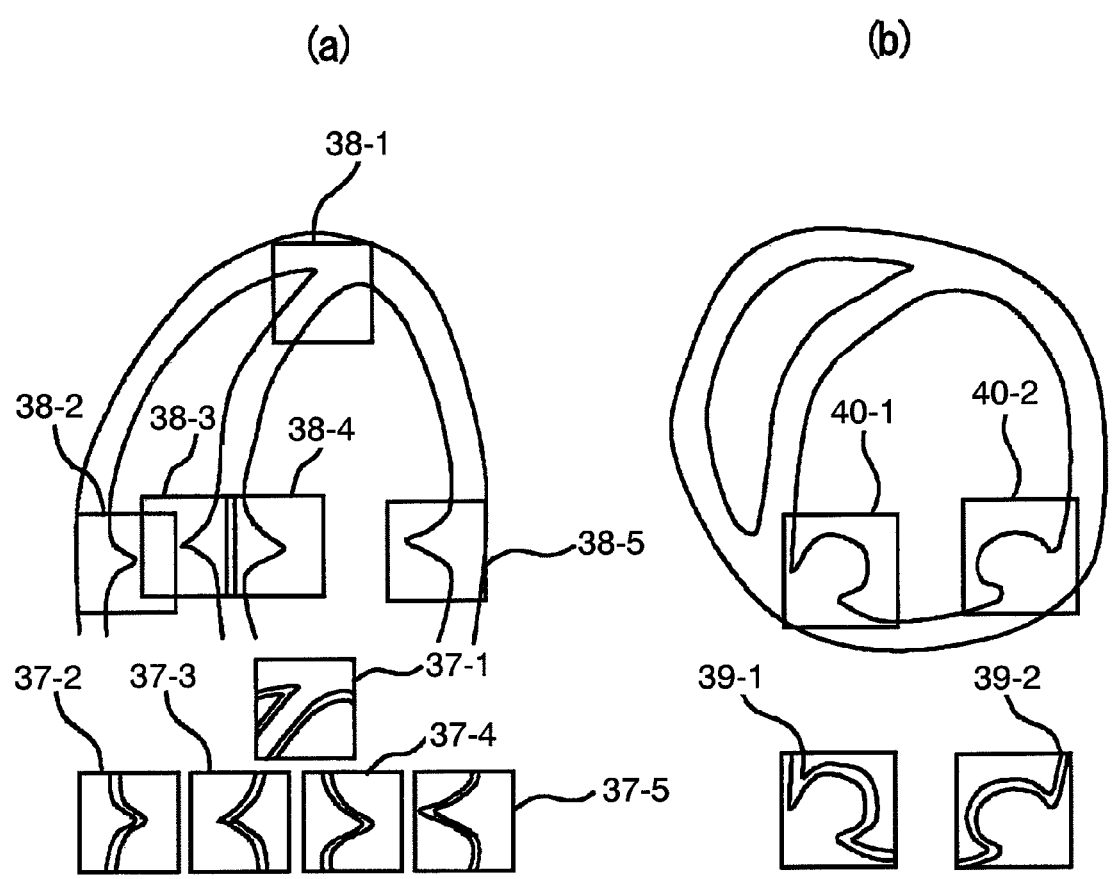
FIG. 12 is a diagram showing a boundary extracting filter for properly extracting a boundary position from a four-chamber view or short-axis view of a heart.

Furthermore, it is desired that the boundary extraction filter to be set is set so as to reflect the boundary shape of the target site. The boundary extracting filter having the shape as shown in FIG. 7 or 9 may be used, however, when an expected boundary is bent or a specific portion of a heart or the like is extracted, a boundary extraction filter having a shape as shown in FIG. 11 or 12 may be used in connection with the situation. In FIG. 11, 36-1 and 36-2 represent two areas constituting a boundary extraction filter, and the area of the gap sandwiched between the two areas is set to be bent in accordance with the bending of an estimated boundary.

FIG. 12(*a*) is a diagram showing a four-chamber view of a heart. The filters represented by 37-1 to 37-5 are used to properly extract boundary positions of places 38-1 to 38-5 of the four-chamber view of the heart. Furthermore, FIG. 12(*b*) is a diagram showing a short-axis view of a heart. The filters represented by 39-1, 39-2 are used to properly extract the boundary positions of places 40-1 to 40-2 of the short-axis view of the heart. When the characterizing portion of the heart is extracted as described above, a filter having the shape of a structure such as a cardiac valve or a papillary area which is characterized in shape may be created. If the contour of the heart or the like can be properly extracted by using the boundary extraction filter as shown in FIG. 12, it can be prevented that the contour of a cavity is inwardly blurred and the value of the volume of the cavity is underestimated when the volume of the cavity of the heart is measured or the like.

Embodiment 2

Figure 13:
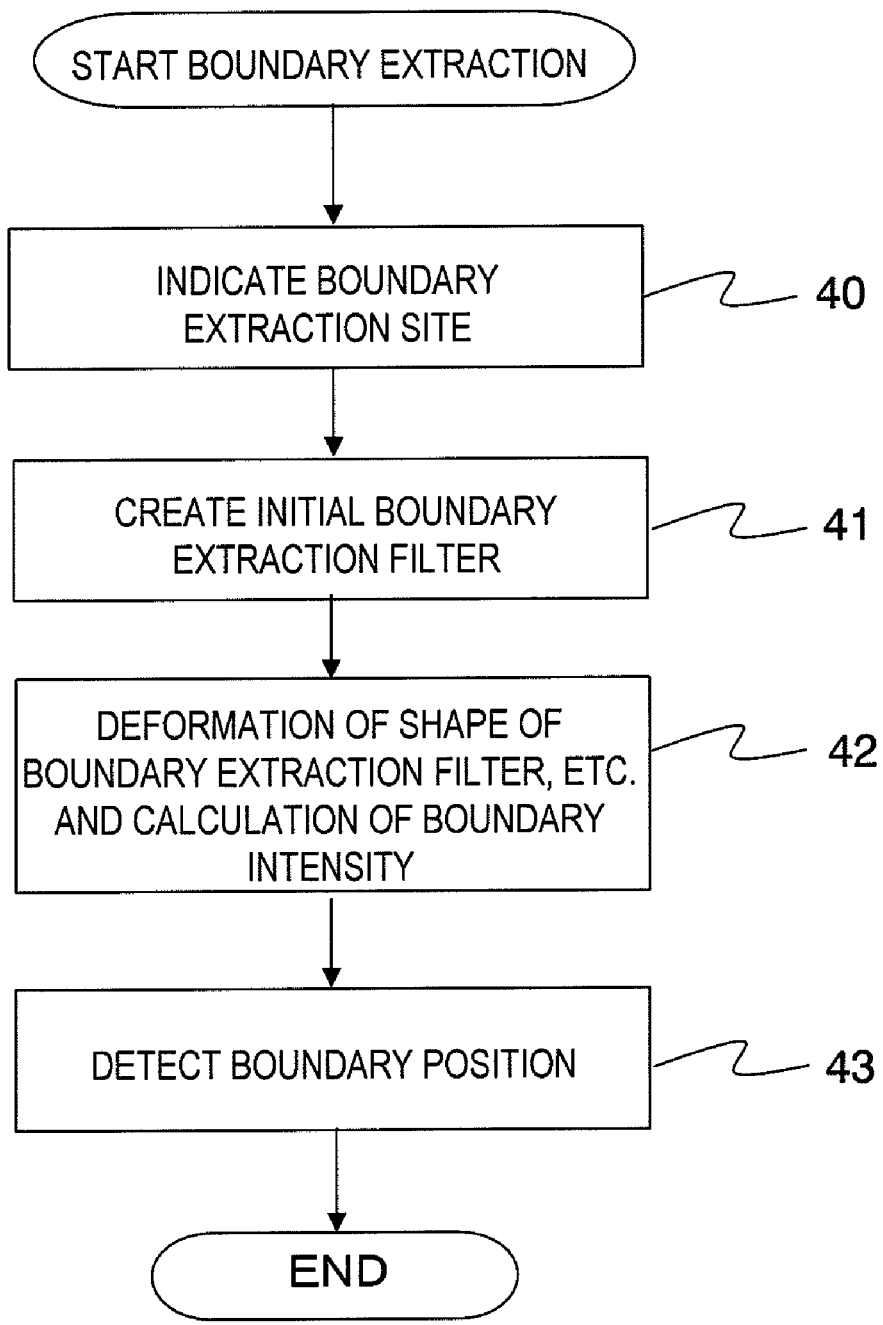
FIG. 13 is a flowchart of a boundary extraction processing of an embodiment 2.

Next, an embodiment 2 according to the present invention will be described with reference to FIGS. 13 to 15. The embodiment 2 is an example in which the boundary position is extracted in a searching style by using the boundary extraction filter according to the present invention when the blurring width of the image or the information concerning the shape of the boundary as an extraction target is unknown or calculation is impossible for some reason.

For example, when the distribution of speckles in the target area of the obtained image is not uniform, the size of the speckles cannot be accurately calculated because the statistical property of the speckle itself is not reflected by the density cooccurrence matrix or the autocorrelation function. In such a case, the boundary position can be searched according to the flowchart of FIG. 13. The respective steps of the flowchart of FIG. 13 will be successively described.

(Step 40)

First, the ultrasonographic device indicates a boundary extraction site manually or automatically by the boundary extraction site indicating means 7.

(Step 41)

Subsequently, in this embodiment, since the blurring width or the shape on the ultrasonic image is unknown, a boundary extracting filter which comprises two areas and has a properly initial shape is created by the filter shape creating/deforming means 11.

(Step 42)

Subsequently, the boundary intensity is successively calculated by the method described with reference to the step 23 while varying some of the interval between the filter areas, the shape, the position and the gradient of the boundary extraction filter comprising the two areas indicated in step 41, thereby determining the distribution of the boundary intensity.

Figure 14:
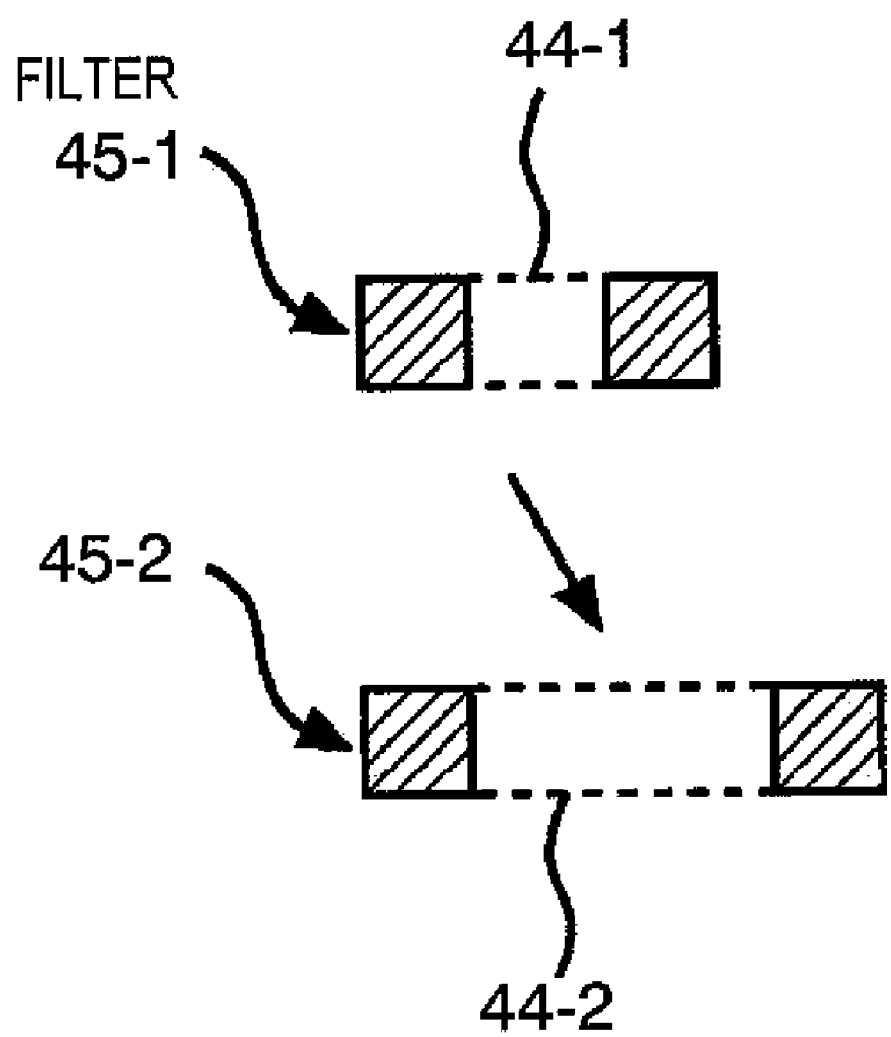
FIG. 14 is a diagram showing an example when the interval between two filter areas is varied without changing the shapes of the two filter areas.

For example, FIG. 14 is a diagram showing an example in which the interval between the two filter areas is varied without changing the shapes of the two filter areas. When the boundary intensity is successively calculated in this step while varying the interval between the filter areas, the interval between the filter areas is varied from 44-1 to 44-2, and the boundary extraction filter is also changed from 45-1 to 45-2.

FIG. 15 is a diagram showing an example in which the shapes of the two filters are changed. In the example of FIG. 15, the shapes of the confronting sides of the two filter areas are successively changed in order of 46-1, 46-2 and 46-3, and a boundary extraction filter which is most fitted to the bending of the boundary line as an extraction target can be searched.

(Step 43)

In step 40, the boundary intensity is calculated while varying some of the interval between the filter areas, the shape, the position and the gradient of the boundary extraction filter, and the interval between the filter areas, the shape and the position which provide the maximum boundary intensity are determined. When the interval between the filter areas is coincident with the blurring width of the target area of the ultrasonic image, the shape is coincident with the shape of the boundary to be extracted and the position is coincident with the position of the boundary to be extracted, the boundary intensity is maximum and thus the position of the boundary is extracted.

In a case where the interval between the filter areas is varied, when the interval between the filter areas is varied from a small one to a larger one, the boundary intensity gradually increases until the size of the interval between the filter areas is coincident with the blurring width. However, when the boundary intensity increases to some degree or more, the boundary intensity does not further increase. Accordingly, when the boundary intensity is calculated while the interval between the filter areas is changed, it is estimated to be better that the interval between the filter areas is varied from a smaller one to a larger one, the interval at which the value of the boundary intensity starts to be saturated at the maximum value is searched, and the boundary position is detected on the basis of the interval concerned.

According to this embodiment, when the blurring width of the image or the information concerning the shape of the boundary as an extraction target is unknown, or when the calculation is impossible for some reason, the actual boundary position can be detected by scanning the image while changing some of the boundary extraction filter, the interval between the filter areas, the shape and the position and searching the position at which the boundary intensity is maximum.

Furthermore, the physical quantities such as the size, etc. of the target area can be accurately calculated by using the coordinates of the calculated actual boundary positions, and accurate ultrasonography can be performed by using the values of the physical quantities.

The present invention is not limited to the above embodiments, and various modifications may be executed without departing from the subject matter of the present invention. For example, the present invention is not limited to the ultrasonographic device, but also applicable to image measurement which is performed offline on an electrical computer such as a personal computer or the like. In FIG. 7, the boundary extraction filter comprises two rectangular areas, however, it may comprise areas having a circular shape. The size of the two areas may be arbitrary, and it may be an area comprising a small number of pixels. Furthermore, the distance corresponding to the half value of the width (the length in the major axis or the minor axis) of the ellipse with which the speckle determined in step 21 is approximated is set as the blurring width, and used to create the boundary extraction filter in step 22. However, it is needless to say that the distance corresponding to any value other than the half value may be calculated as the blurring width in accordance with the property or the like of the speckle concerned. Furthermore, the parameter used as the boundary intensity may be the separability indicated by the equations (1) to (3). However, it is needless to say that any index representing the difference degree between the image data contained in the two areas may be used, or an index based on another calculation method may be used.

The invention claimed is:

1. An ultrasonographic device having an ultrasonic probe for transmitting/receiving an ultrasonic wave to an examinee, image generating means which is connected to the ultrasonic probe and generates an ultrasonic image on the basis of an ultrasonic signal obtained by the ultrasonic probe, a controller which is connected to the ultrasonic probe and the image generating means to control the ultrasonic probe and the image generating means, and display means which is connected to the image generating means and the controller and displays the ultrasonic image generated by the image generating means under the control of the controller, characterized by further comprising selecting means for selecting a site for detecting the position of a boundary of an organ of the examinee on the image displayed on the display means, boundary extracting filter setting means for setting a boundary extracting filter comprising two areas which are spaced from each other at a predetermined interval on the ultrasonic image, and boundary position detecting means for analyzing pixel data within the boundary extracting filter set by the boundary extracting filter setting means in the neighborhood of the site selected by the selecting means to detect the position of the boundary, the boundary position detected by the boundary position detecting means being displayed on the display means under the control of the controller.

2. The ultrasonographic device according to claim 1, further comprising boundary intensity calculating means for analyzing pixel values within the two areas are while the boundary extracting filter set by the boundary extracting filter setting means is varied in position and/or gradient in the neighborhood of the site selected by the selecting means, thereby determining a boundary intensity, wherein the boundary position detecting means determines a position and/or a gradient of the boundary extraction filter at which the boundary intensity is maximum or a predetermined value or more, thereby detecting the position of the boundary.

3. The ultrasonographic device according to claim 2, wherein an index representing the difference degree between pixel data contained in the two areas is used as the boundary intensity.

4. The ultrasonographic device according to claim 2, wherein the boundary intensity is the separability obtained by dividing an interclass variance by a total variance, the interclass variance being obtained by averaging the pixel data within the two areas every area and then calculating a variance value, and the total variance being obtained by calculating a variance value by directly using the pixel data within the two areas.

5. The ultrasonographic device according to claim 2, wherein the boundary extraction filter set by the boundary extraction filter setting means is changeable in the interval between the two areas, shape, position or gradient, the boundary intensity calculating means successively calculates the boundary intensity while changing the interval between the two areas, the shape, the position or the gradient, and the boundary position detecting means detects the position of the boundary on the basis of the interval between the two areas, the shape, the position or the gradient at which the boundary intensity is maximum.

6. The ultrasonographic device according to claim 1, wherein the two areas comprise two areas at a higher pixel-value side and a lower pixel-value side, on the basis of information of a position and/or gradient of the boundary extraction filter at which the boundary intensity is maximum, the boundary position detecting means sets, as the position of the boundary, an edge which faces the low pixel-value side out of the surrounding area surrounding the area at the higher pixel-value side at the position concerned.

7. The ultrasonographic device according to claim 1, further comprising organ measuring means for calculating the area of the area surrounded by the boundary or the volume of an organ representing the area surrounded by the boundary on the basis of the boundary position determined by the boundary position extracting means.

8. The ultrasonographic device according to claim 1, further comprising blurring width calculating means for calculating a blurring width on the ultrasonic image at the site selected by the selecting means, wherein the boundary extraction filter setting means determines the interval between the two areas on the basis of the blurring width calculated by the blurring width calculating means.

9. The ultrasonographic device according to claim 8, wherein the two areas have rectangular shapes, and the boundary extraction filter setting means sets the distance between confronting sides of the two areas so that the distance is equal to the blurring width.

10. The ultrasonographic device according to claim 8, wherein the two areas comprise a ring-shaped area at the outside and a circular shaped area at the inside, and the boundary extraction filter setting means sets the width of a gap sandwiched between the two areas so that the width is equal to the blurring width.

11. The ultrasonographic device according to claim 8, wherein the shapes of the two areas by the boundary extraction filter setting means are made to reflect the shape of the boundary of a target site to be extracted.

12. The ultrasonographic device according to claim 8, wherein the blurring width calculating means determines the size of the ellipse every depth in accordance with variation of the size of the speckle in accordance with the depth in the ultrasonic wave transmission/reception direction on the ultrasonic image, thereby calculating the blurring width, and the boundary extraction filter setting means sets a boundary extracting filter whose interval is varied in conformity with the variation of the size of the speckle in accordance with the depth.

13. The ultrasonographic device according to claim 8, wherein the two areas are circular in shape and set to be spaced from each other at the distance corresponding to the blurring width.

14. The ultrasonographic device according to claim 8, wherein the blurring width calculating means calculates the blurring width on the image by texture analysis.

15. The ultrasonographic device according to claim 14, wherein the texture analysis is executed by calculating a density cooccurrence matrix or an autocorrelation function with the image data of the ultrasonic image.

16. The ultrasonographic device according to claim 14, wherein the blurring width calculating means approximates a speckle appearing on the ultrasonic image by the shape of an ellipse, and determines the size of the ellipse to thereby calculate the blurring width.

17. The ultrasonographic device according to claim 16, wherein the distance of the half value of the length in the minor axis or major axis of the speckle-approximating ellipse is calculated as the blurring width.

18. The ultrasonographic device according to claim 14, wherein the blurring width calculating means executes the texture analysis in consideration of the direction on the ultrasonic image of the speckle which varies in accordance with the type of the ultrasonic probe.

19. The ultrasonographic device according to claim 16, wherein when the ultrasonic probe is a linear type, the blurring width calculating means sets the direction of the minor axis or the major axis of the ellipse for approximating the speckle to a vertical direction or a horizontal direction on the screen of the display means, and when the ultrasonic probe is a sector type, the direction of the ultrasonic wave beam is set to the minor axis or the major axis of the ellipse.

20. An ultrasonographic method that can extract the position of a boundary of an organ displayed on an ultrasonic image comprising:
  (1) a step of indicating a site for extracting the boundary on the ultrasonic image;
  (2) a step of calculating a blurring width of an image in the neighborhood of the site set in the step (1);
  (3) a step of setting as a boundary extracting filter two areas having a gap corresponding to the blurring width calculated in the step (2);
  (4) a step of determining the intensity of the boundary by analyzing pixel values in the two areas while varying the position and/or gradient of the boundary extracting filter set in the step (3);
  (5) a step of extracting the position of the boundary by determining the position and/or gradient at which the boundary intensity is maximum in the step (4); and
  (6) a step of calculating the area of an area surrounded by the boundary or the volume of an organ representing an area surrounded by the boundary on the basis of the boundary position determined in the step (5).

* * * * *